(12) United States Patent
San et al.

(10) Patent No.: US 8,795,991 B2
(45) Date of Patent: Aug. 5, 2014

(54) INCREASING BACTERIAL SUCCINATE PRODUCTIVITY

(75) Inventors: Ka-Yiu San, Houston, TX (US); George Bennett, Houston, TX (US); Grant Balzer, Houston, TX (US); Jiangfeng Zhu, Houston, TX (US); Chandresh Thakker, Houston, TX (US); Ailen Sanchez, Foster City, CA (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 13/696,268

(22) PCT Filed: May 3, 2011

(86) PCT No.: PCT/US2011/035001
§ 371 (c)(1),
(2), (4) Date: Jan. 14, 2013

(87) PCT Pub. No.: WO2011/140088
PCT Pub. Date: Nov. 10, 2011

(65) Prior Publication Data
US 2013/0203137 A1    Aug. 8, 2013

Related U.S. Application Data

(60) Provisional application No. 61/332,427, filed on May 7, 2010.

(51) Int. Cl.
*C12N 15/70*    (2006.01)
(52) U.S. Cl.
USPC ........................................ 435/145; 435/252.3
(58) Field of Classification Search
CPC ............ C12N 9/18; C12N 9/2437; C12N 9/54
USPC ........................................................ 435/135
See application file for complete search history.

(56) References Cited

U.S. PATENT DOCUMENTS

| | | | |
|---|---|---|---|
| 7,223,567 B2 | 5/2007 | Ka-Yiu | |
| 2005/0042736 A1 | 2/2005 | San et al. | |
| 2006/0046288 A1 | 3/2006 | Ka-Yiu et al. | |
| 2010/0086958 A1 | 4/2010 | Davis et al. | |
| 2013/0029378 A1* | 1/2013 | Davis et al. | 435/90 |

FOREIGN PATENT DOCUMENTS

WO  PCT/US2011/035001    9/2011

OTHER PUBLICATIONS

Jantama et al., Combining Metabolic Engineering and Metabolic Evolution to Develop Nonrecombinant Strains of *Escherichia coli* C That Produce Succinate and Malate. Biotechnology and Bioengineering. vol. 99, No. 5, 1140-1154. Apr. 1, 2008.*
McKinlay et al., Prospects for a bio-based succinate industry. Appl. Microbiol. Biotechnol. 76:727-740, 2007.*
Sanchez, A.M., Bennett, G.N., San, K.-Y., 2005. Novel pathway engineering design of the anaerobic central metabolic pathway in *Escherichia coli* to increase succinate yield and productivity. Metab. Eng. 7, 229-239.
Berrios-Rivera, S.J., Bennett, G.N., San, K.-Y., 2002a. Metabolic engineering of *Escherichia coli*: increase of NADH availability by overexpressing an NAD+– dependent formate dehydrogenase. Metab. Eng. 4, 217-229.
Berrios-Rivera, S.J., Bennett, G.N., San, K.-Y., 2002b. The effect of increasing NADH availability on the redistribution of metabolic fluxes in *Escherichia coli* chemostat cultures. Metab. Eng. 4, 230-237.
Berrios-Rivera, S.J., Sanchez, A.M., Bennett, G.N., San, K.-Y., 2004 Effect of different levels of NADH availability on metabolite distribution in *Escherichia coli* fermentation in defined and complex media. App. Microbiol. Biotechnol. 65, 426-432.
Lin H., San, K.-Y., Bennett, G.N. 2005. Effect of *Sorghum vulgare* phosphoenolpyruvate carboxylase and *Lactococcus lactis* pyruvate carboxylase coexpression on succinate production in mutant strains of *Escherichia coli*. Appl. Microbiol. Biotechnol. 67, 515-523.
Sakai, Y., Murdanato, A.P., Konishi, T., Iwamatsu, A., Kato, N., 1997. Regulation of the formate dehydrogenase gene, FDH1, in the methylotrophic yeast *Candida boidinii* and growth characteristics of an FDH1-disrupted strain on methanol, methylamine, and choline. J. Bacteriol. 179, 4480-4485.
Vemuri, G.N., Eiteman, M.A., Altman, E., 2002. Effects of growth mode and pyruvate carboxylase on succinic acid production by metabolically engineered strains of *Escherichia coli*. Appl. Environ. Microbiol. 68, 1715-1727.

* cited by examiner

*Primary Examiner* — Tekchand Saidha
*Assistant Examiner* — Rama P Ramanujam
(74) *Attorney, Agent, or Firm* — Boulware & Valoir

(57) ABSTRACT

Improved bacteria for making succinate and other 4 carbon dicarboxylates from the Krebs cycle have modifications to reduce acetate, lactate, EtOH and formate, as well as turn on the glyoxylate shunt, produce more NADH and overexpress In one embodiment, the bacteria are ΔadhEΔldhAΔiclRΔack-pta plus PYC+ and NAD+-dependant FDH+.

17 Claims, 8 Drawing Sheets

LEGEND for FIG 3A-B.

SBS550MG pHL413Kan = $\Delta adhE\Delta ldhA\Delta iclR\Delta ack\text{-}pta$ plus $PYC^+$ SBS550MG pHL413KF12 = $\Delta adhE\Delta ldhA\Delta iclR\Delta ack\text{-}pta$ plus $PYC^+$, $FDH^+$

FIGURE 4A

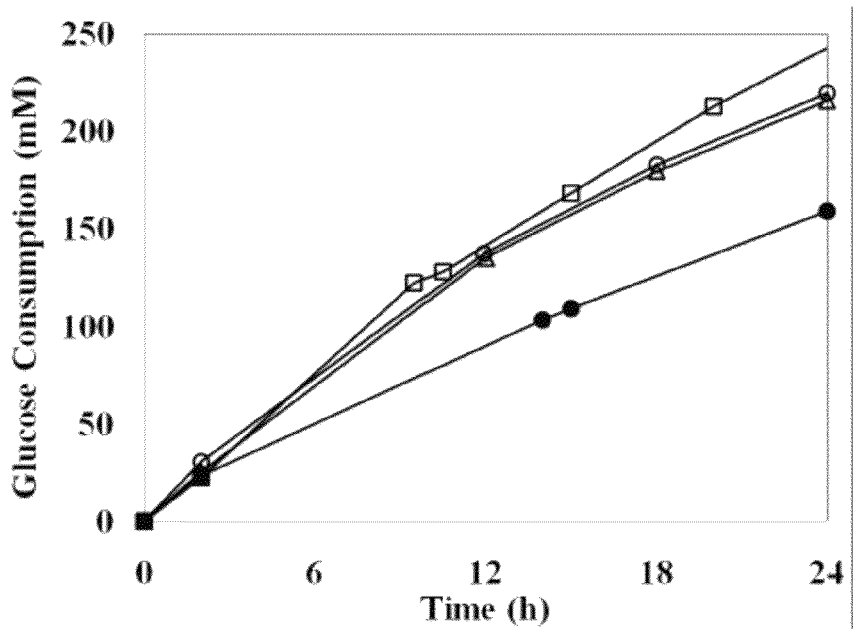

FIGURE 4B

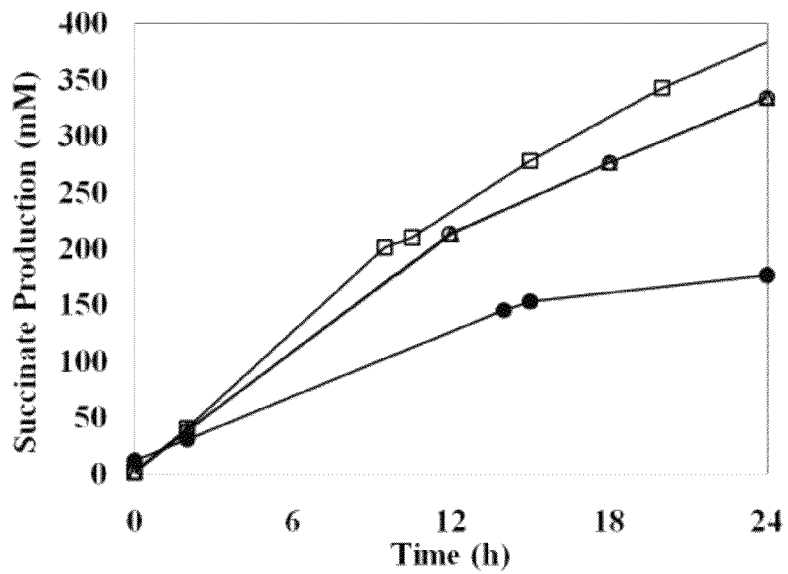

LEGEND for FIG 4A-B.

● = $\Delta adhE \Delta ldhA \Delta iclR \Delta ack$-$pta$ plus $PYC^+$

○ = $\Delta adhE \Delta ldhA \Delta iclR \Delta ack$-$pta$ plus $PYC^+$, $FDH^+$ (first replicate)

Δ = $\Delta adhE \Delta ldhA \Delta iclR \Delta ack$-$pta$ plus $PYC^+$, $FDH^+$ (second replicate)

□ = $\Delta adhE \Delta ldhA \Delta iclR \Delta ack$-$pta$ plus $PYC^+$, $FDH^+$ plus 6 g/L glucose in the aerobic phase

FIGURE 5A

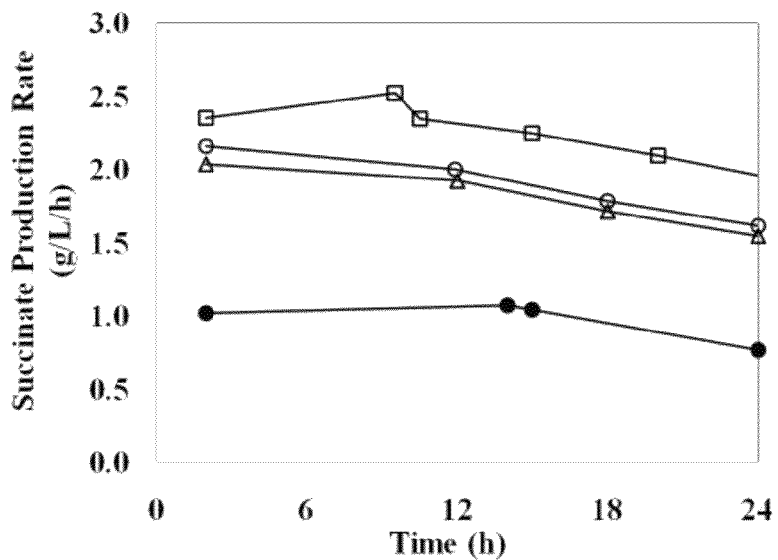

FIGURE 5B

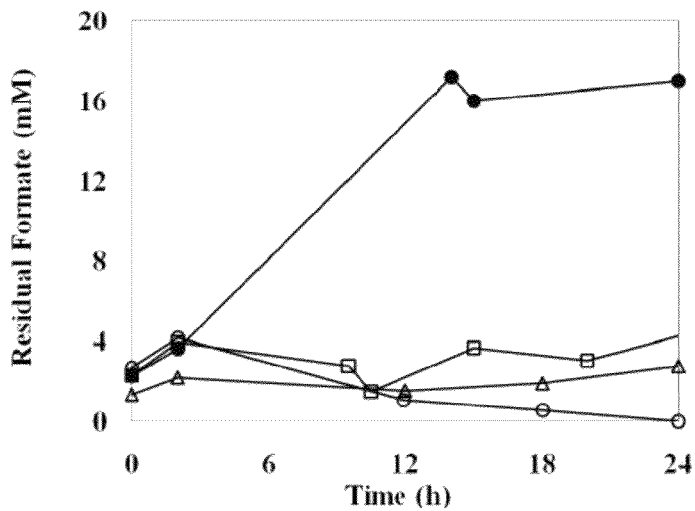

LEGEND for FIG 5A-B.

● = $\Delta adhE\Delta ldhA\Delta iclR\Delta ack\text{-}pta$ plus $PYC^+$

○ = $\Delta adhE\Delta ldhA\Delta iclR\Delta ack\text{-}pta$ plus $PYC^+$, $FDH^+$ (first replicate)

Δ = $\Delta adhE\Delta ldhA\Delta iclR\Delta ack\text{-}pta$ plus $PYC^+$, $FDH^+$ (second replicate)

□ = $\Delta adhE\Delta ldhA\Delta iclR\Delta ack\text{-}pta$ plus $PYC^+$, $FDH^+$ plus 6 g/L glucose in the aerobic phase LEGEND for FIG 6A-B.

SBS550MG pHL413Kan = $\Delta adhE \Delta ldhA \Delta iclR \Delta ack$-$pta$ plus PYC$^+$ SBS550MG pHL413KF12 = $\Delta adhE \Delta ldhA \Delta iclR \Delta ack$-$pta$ plus PYC$^+$, FDH$^+$

FIGURE 7

```
  1  MKIVLVLYDA  GKHAADEEKL  YGCTENKLGI  ANWLKDQGHE  LITTSDKEGG  NSVLDQHIPD
 61  ADIIITTPFH  PAYITKERID  KAKKLKLVVV  AGVGSDHIDL  DYINQTGKKI  SVLEVTGSNV
121  VSVAEHVVMT  MLVLVRNFVP  AHEQIINHDW  EVAAIAKDAY  DIEGKTIATI  GAGRIGYRVL
181  ERLVPFNPKE  LLYYDYQALP  KDAEEKVGAR  RVENIEELVA  QADIVTVNAP  LHAGTKGLIN
241  KELLSKFKKG  AWLVNTARGA  ICVAEDVAAA  LESGQLRGYG  GDVWFPQPAP  KDHPWRDMRN
301  KYGAGNAMTP  HYSGTTLDAQ  TRYAQGTKNI  LESFFTGKFD  YRPQDIILLN  GEYVTKAYGK
361  HDKK
```

SEQ ID NO 1: formate dehydrogenase from *Candida boidinii*, GenBank Accession number CAA09466. Other sequences that can be used include XP_506003.1 [*Yarrowia lipolytica* 70-72% identity]; XP_462381.1 [*Debaryomyces hansenii* CBS767 65-66%]; and XP_003071148.1 [*Coccidioides posadasii* C735 delta SOWgp 64%], among others.

FIGURE 8

```
  1 MKKLLVANRG EIAVRVFRAC NELGLSTVAV YAREDEYSVH RFKADESYLI GQGKKPIDAY
 61 LDIDDIIRVA LESGADAIHP GYGLLSENLE FATKVRAAGL VFVGPELHHL DIFGDKIKAK
121 AAADEAQVPG IPGTNGAVDI DGALEFAQTY GYPVMIKAAL GGGGRGMRVA RNDAEMHDGY
181 ARAKSEAIGA FGSGEIYVEK YIENPKHIEV QILGDSHGNI VHLHERDCSV QRRNQKVIEI
241 APAVGLSPEF RNEICEAAVK LCKNVGYVNA GTVEFLVKDD KFYFIEVNPR VQVEHTITEL
301 ITGVDIVQAQ ILIAQGKDLH TEIGIPAQAE IPLLGSAIQC RITTEDPQNG FLPDTGKIDT
361 YRSPGGFGIR LDVGNAYAGY EVTPYFDSLL VKVCTFANEF SDSVRKMDRV LHEFRIRGVK
421 TNIPFLINVI ANENFTSGQA TTTFIDNTPS LFNFPRLRDR GTKTLHYLSM ITVNGFPGIE
481 NTEKRHFEEP RQPLLNIEKK KTAKNILDEQ GADAVVEYVK NTKEVLLTDT TLRDAHQSLL
541 ATRLRLQDMK GIAQAIDQGL PELFSAEMWG GATFDVAYRF LNESPWYRLR KLRKLMPNTM
601 FQMLFRGSNA VGYQNYPDNV IEEFIHVAAH EGIDVFRIFD SLNWLPQMEK SIQAVRDNGK
661 IAEATICYTG DILDPSRPKY NIQYYKDLAK ELEATGAHIL AVKDMAGLLK PQAAYRLISE
721 LKDTVDLPIH LHTHDTSGNG IITYSGATQA GVDIIDVATA SLAGGTSQPS MQSIYYALEH
781 GPRHASINVK NAEQIDHYWE DVRKYYAPFE AGITSPQTEV YMHEMPGGQY TNLKSQAAAV
841 GLGHRFDEIK QMYRKVNMMF GDIIKVTPSS KVVGDMALFM IQNELTEEDV YARGNELNFP
901 ESVVSFFRGD LGQPVGGFPE ELQKIIVKDK SVIMDRPGLH AEKVDFATVK ADLEQKIGYE
961 PGDHEVISYI MYPQVFLDYQ KMQREFGAVT LLDTPTFLHG MRLNEKIEVQ IEKGKTLSIR
1021 LDEIGEPDLA GNRVLFFNLN GQRREVVIND QSVQTQIVAK RKAETGNPNQ IGATMPGSVL
1081 EILVKAGDKV KKGQALMVTE AMKMETTIES PFDGEVIALH VVKGEAIQTQ DLLIEID
```

SEQ ID NO: 2: AF068759 pyruvate carboxylase [Lactococcus lactis]. See also ZP_00604270.1 [Enterococcus faecium 72% identity]; ZP_05581847.1 [Enterococcus faecalis 70%]; ZP_05645624.1 [Enterococcus casseliflavus 70%]; ZP_02184755.1 [Carnobacterium 68%]; ZP_07895867.1 [Enterococcus italicus 68%]; YP_001375878.1 [Bacillus cereus 63%]; EFR91190.1 [Listeria innocua 63%]; ZP_05228659.1 [Listeria monocytogenes 63%]; ZP_04092026.1 e [Bacillus thuringiensis 63%]

US 8,795,991 B2

INCREASING BACTERIAL SUCCINATE PRODUCTIVITY

PRIOR RELATED APPLICATIONS

This invention is a National Phase filing under 35 U.S.C. §371 of International Application PCT/US11/35001, filed on May 3, 2011 which claims priority to U.S. 61/332,427, filed on May 7, 2010. Both applications are incorporated by reference in their entirety herein.

FEDERALLY SPONSORED RESEARCH STATEMENT

This invention was made with government support under Grant No: BES 0000303 awarded by the NSF. The government has certain rights in the invention.

REFERENCE TO MICROFICHE APPENDIX

Not applicable.

FIELD OF THE INVENTION

Engineered bacteria that produce higher levels of 4-carbon dicarboxylic acids from the Krebs Cycle, especially succinate, and methods and uses for same.

BACKGROUND OF THE INVENTION

Succinate has many industrial uses. As a specialty chemical, it is a flavor and formulating ingredient in food processing, a pharmaceutical ingredient, and a surfactant. Succinate's greatest market potential, though, would be its use as an intermediary commodity chemical feedstock for producing bulk chemicals, stronger-than-steel plastics, ethylene diamine disuccinate (a biodegradable chelator), and diethyl succinate (a green solvent for replacement of methylene chloride). Along with succinic acid, other 4-carbon dicarboxylic acids from the Krebs Cycle, such as malic acid and fumaric acid, also have feedstock potential.

More than 17,000 tons of succinate are sold per year. It is currently sold in the U.S. for $2.70-4.00/lb, depending on its purity. Succinate is currently produced petrochemically from butane through maleic anhydride. It can also be made by fermentation from glucose at a production cost of about $1.00/lb, but for succinate to be competitive with maleic anhydride as a commodity chemical, its overall production cost should be lowered to approximately 15 cents/lb.

The production of succinate, malate, and fumarate from glucose, xylose, sorbitol, and other "green" renewable feedstocks (in this case through fermentation processes) is a way to supplant the more energy intensive methods of deriving such acids from nonrenewable sources.

Succinate is an intermediate for anaerobic fermentations by propionate producing bacteria (e.g., *Actinobacillus succinogenes*), but those processes result in low yields and concentrations and these bacteria are generally not cost effective to use.

It has long been known that mixtures of acids are produced from *E. coli* fermentation. However, for each mole of glucose fermented, only 1.2 moles of formic acid, 0.1-0.2 moles of lactic acid, and 0.3-0.4 moles of succinic acid are produced. As such, efforts to produce carboxylic acids fermentatively have resulted in relatively large amounts of growth substrates, such as glucose, not being converted to desired product, and this greatly reduces the cost effectiveness of the method.

Metabolic engineering has the potential to considerably improve bacterial productivity by manipulating the throughput of metabolic pathways. Specifically, manipulating enzyme levels through the amplification, addition, or deletion of a particular pathway can result in high yields of a desired product. Several examples of increasing succinate levels through metabolic engineering are known, including several patented examples from our own group. However, there is always room for continued improvement.

What is needed in the art is an improved bacterial strain that produces higher levels of succinate and other carboxylic acids than heretofor provided.

SUMMARY OF THE INVENTION

The present invention establishes an improved in vivo method for production of succinic acid that increases the yield, and the production rate of succinate and other components of the Krebs cycle, and reduces the byproduct formate.

Generally speaking, the invention includes recombinant bacteria engineered to produce fewer by products (acetate, lactate, EtOH), balancing the carbon flux through the fermentative pathway and the glyoxylate cycle (which has less NADH requirement), as well as driving the Krebs cycle through increased expression of PYC and supplying increased NADH through overexpression of FDH, which also has the effect of reducing the byproduct formate.

Thus, genes encoding proteins essential for the production of lactate, acetate and ethanol are disrupted and the glyoxylate cycle is turned on. The glyoxylate cycle (aka glyoxylate shunt or bypass) like the citric acid cycle, begins with the condensation of acetyl CoA and oxaloacetate to form citrate, which is then isomerized to isocitrate. Instead of being decarboxylated, isocitrate is cleaved by isocitrate lyase into succinate and glyoxylate. The subsequent steps regenerate oxaloacetate from glyoxylate. Acetyl CoA condenses with glyoxylate to form malate in a reaction catalyzed by malate synthase, which resembles citrate synthase. Finally, malate is oxidized to oxaloacetate, as in the citric acid cycle. The sum of these reactions of the glyoxylate-TCA pathway is:

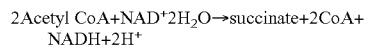

$$2\text{Acetyl CoA} + \text{NAD}^+ 2\text{H}_2\text{O} \rightarrow \text{succinate} + 2\text{CoA} + \text{NADH} + 2\text{H}^+$$

Thus, using the glyoxylate cycle, allows conversion of acetate to succinate and reduces the requirements for NADH. Additional NADH is produced with the added FDH, which also reduces formate byproduct.

Thus, such bacteria have disrupted alcohol dehydrogenase (thus producing less EtOH), disrupted lactate dehydrogenase (thus producing less lactate), disrupted acetate kinase or phosphotransacetylase or both ack-pta (thus producing less acetate), a disruption in iclR (thus allowing expression of aceBAK and operation of the glyoxylate shunt to utilize acetate to make succinate) and overexpression of NAD+ dependent FDH (thus producing needed NADH and reducing formate) and overexpressed PYC (further driving the Kreb's cycle).

In a preferred embodiment, the invention is *E. coli* comprising a disruption in adhE, a disruption in ldh, a disruption in ack-pta, a disruption in iclR and overexpression of both FDH and PYC.

The invention also includes methods employing such bacteria, including methods of making succinate and other components of the TCA cycle, such as citrate, alpha-ketoglutarate, fumarate, malate and oxaloacetate.

In more detail, one embodiment of the invention is a bacteria comprising reduced activity of alcohol hydrogenase (ADH), reduced activity of lactate dehydrogenase (LDH), reduced activity of acetate kinase or phosphotransacetylase or both, reduced activity of the aceBAK operon repressor (ICLR) and overexpression of NAD⁺-dependent formate dehydrogenase (FDH) and overexpression of pyruvate carboxylase (PYC). More preferred is *E. coli* bacteria comprising ΔadhE, Δldh, Δack-pta, ΔiclR and FDH⁺ and PYC⁺.

The above bacteria can be used to make any four carbon dicarboxylic acid from the Krebs cycle simply by culturing the bacteria in a medium, and isolating a four carbon dicarboxylic acid from said bacteria or medium or both. In preferred embodiments, the four carbon dicarboxylic acid is succinate, and the medium is supplemented with 25-250 mM formate.

Succinic acid and succinate are used interchangeably herein, as are other acid/base nomenclature for organic acids.

As used herein, "FDH" means a protein having NAD⁺-dependent formate dehydrogenase activity. Many such proteins are available in GenBank and exemplary proteins are described in U.S. Pat. No. 7,256,016, incorporated herein in its entirety by reference. The gene encoding FHD in *Candida* is fdh1, but the gene may have other names in other species.

In the exemplified embodiment the FDH is from *Candida boidinii*, but obviously any functional FDH can be used from any source since by definition FDH is an NAD⁺formate dehydrogenase and will catalyze the same reaction. Thus, the FDH can selected from the group consisting of *Candida boidinii* FDH, *Candida methylica* FDH, *Pseodomonas* sp 101 FDH, *Arabidopsis thaliana* FDH, *Staphylococcus aureus* FDH, *Saccharomyces bayanus* FDH, *Saccharomyces exiguus* FDH, *Saccharomyces servazzii* FDH, *Zygosaccharomyces rouxii* FDH, *Saccharomyces kluyveri* FDH, *Kluyveromyces thermotolerans* FDH, *Kluyveromyces lactis* FDH, *Kluyveromyces marxianus* FDH, *Pichia angusta* FDH, *Debaryomyces hansenii* FDH, *Pichia sorbitophila* FDH, *Candida tropicalis* FDH, and *Yarrowia lipolytica* FDH, among others.

In a preferred embodiment, the FDH has SEQ ID NO. 1 (FIG. 7), but variations having 65-75% identity are found in other species.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli*, or other bacterial species using the codon bias for the species in which the gene will be expressed.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 1 1 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=1 1 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (ncbi.nlm.nih.gov/BLAST/).

As used herein, "ADH" means a protein having alcohol dehydrogenase activity. Many such proteins are available in GenBank. The *E. coli* gene encoding this protein is adhE, but the gene may have other names in other species.

As used herein, "PYC" means pyruvate carboxylase. Many such proteins are available in GenBank. In a preferred embodiment, the pyruvate carboxylase (PYC) is from *Lactococcus lactisis* (SEQ ID NO: 2 of FIG. 8), but other sequences having 60-75% identity are available in a variety of other species. The gene encoding PYC in *Lactococcus is* called pycA, but the gene may have other names in other species.

We have exemplified the invention herein using *E. coli*, but it can easily be performed in other bacteria, including *Bacillus, Lactobacillus, Lactococcus, Clostridia* and the like, provided the bacteria have the same or equivalent pathways to those diagrammed in FIG. 1 such that the same modifications can be made therein. Since the Krebs cycle and the glyoxylate bypass are common in bacteria and plants, the invention is believed to be generally applicable.

As used herein, "LDH" means a protein having lactate dehydrogenase activity. Many such proteins are available in GenBank. The *E. coli* gene encoding this protein is ldhA, but it may have other names in other species.

As used herein, "ADH" means a protein having alcohol dehyrogenase activity. Many such proteins are available in GenBank. The *E. coli* gene encoding this protein is adhE, but it may have other names in other species.

As used herein the aceBAK operon repressor is ICLR and the gene encoding same is iclR, but it may have other names in other species.

The disruptions in ADH, LDH, ACK-PTA and ICLR can be derived as described in U.S. Pat. No. 7,223,567, incorporated herein in its entirety by reference.

Figure 1:
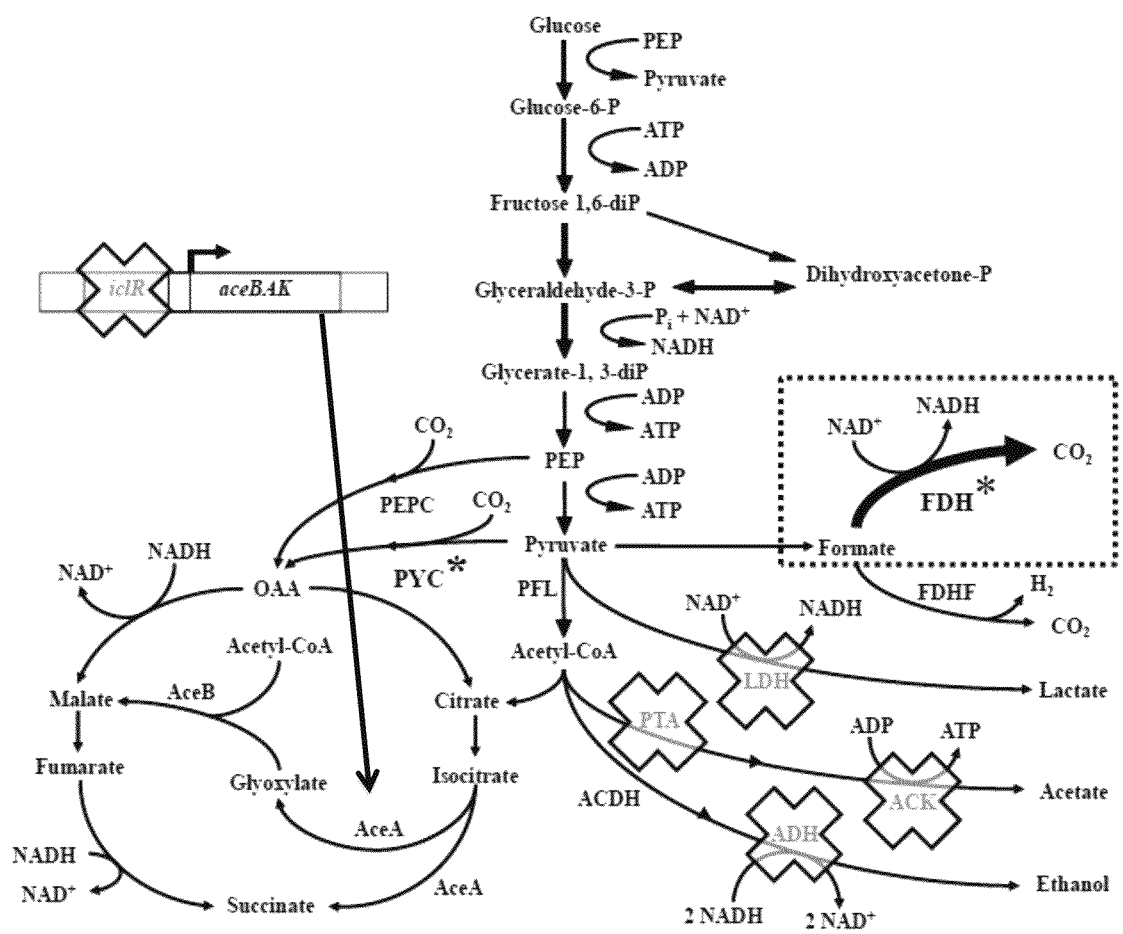
FIG. 1 is a diagram showing the genetically engineered central anaerobic metabolic pathway of *E. coli* strain SBS550MG (ΔadhEΔldhAΔiclRΔack-pta) harboring pHL413KF1 (PYC⁺, FDH⁺).

Shaded X-boxes in FIG. 1 represent inactivated pathways in *E. coli* strain SBS550MG (ΔadhEΔldhAΔiclRΔack-pta) (Sanchez et al., 2005): lactate (LDH), acetate (PTA, ACK), ethanol (ADH), and glyoxylate bypass operon (aceBAK) repressor gene (iclR). The asterisks indicate the overexpressed heterologous enzymes pyruvate carboxylase (PYC) from *Lactococcus lactis* (Lin et al., 2004) and the NAD+-dependent formate dehydrogenase (FDH) from *Candida boidinii*. The bold arrow in the dotted box represents the newly introduced NADH regenerating formate dehydrogenase (FDH) pathway demonstrated herein. The glyoxylate shunt, turned on by deleting iclR, is shown crossing the Kreb's cycle (see straight arrow).

Figure 2:
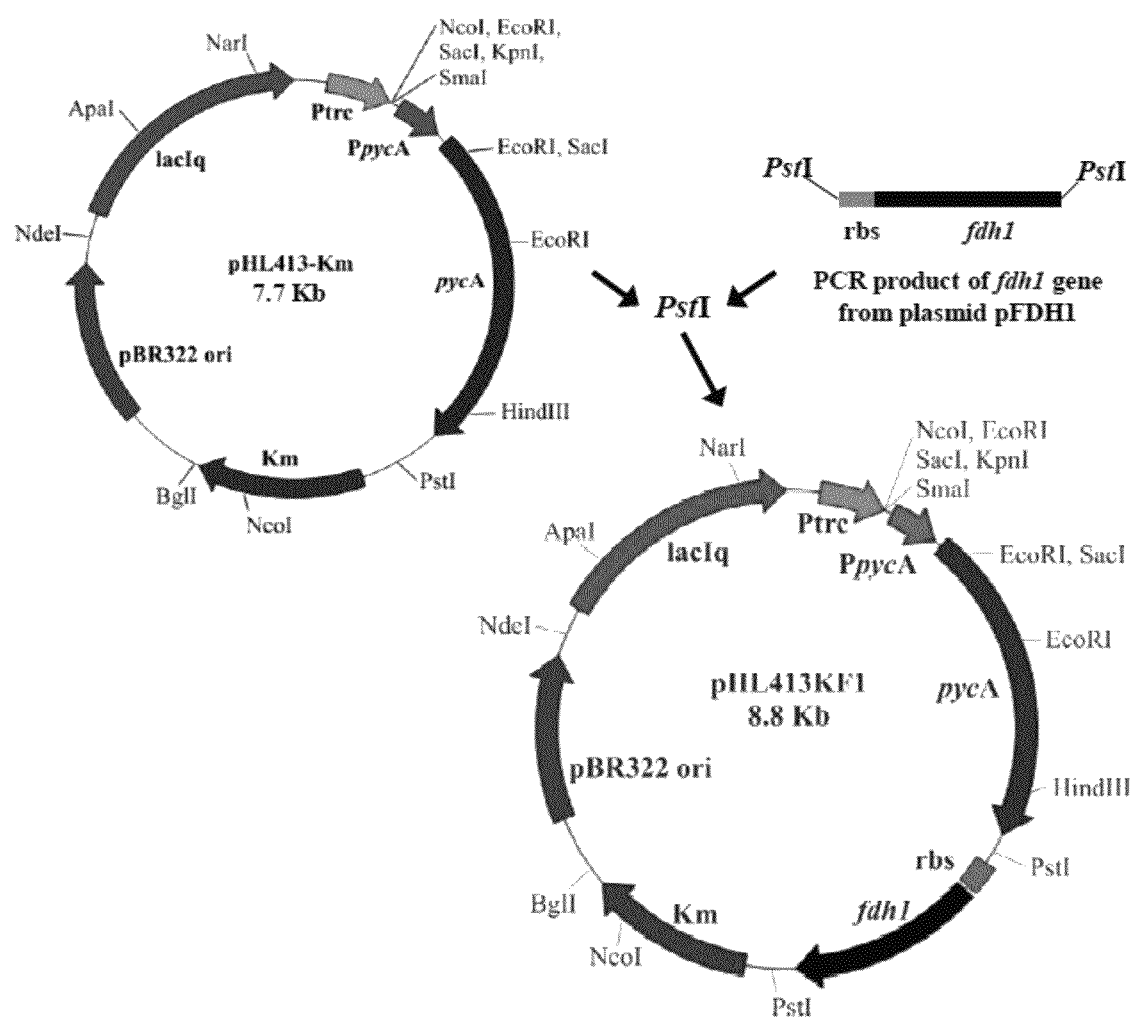

FIG. 2 Schematic diagram showing the construction of pHL413KF1 ((PYC⁺, FDH⁺). The 1.1 Kb fdh1 (*Candida biodinii*) fragment was PCR amplified from pFDH1 (Sakai et al. 1997), restriction digested with PstI, and ligated to the 7.8 Kb PstI restriction digested pHL413Kan (PYC⁺). The newly constructed 8.8 Kb pHL413KF1 (PYC⁺, FDH⁺) co-expresses the heterologous pyruvate carboxylase gene (pycA) from *Lactococcus lactis* and the NAD+-dependent formate dehydrogenase gene (fdh1) from *Candida boidinii*.

Abbreviations in FIG. 2: Ptrc, trc promoter; PpycA, native promoter of the *Lactococcus lactis* pyruvate carboxylase (pycA) gene; Km, kanamycin resistance gene; pBR322 ori, origin of replication; lacIq: lac operon repressor; rbs: ribosome binding site; restriction enzyme sites: NcoI, EcoRI, SacI, KpnI, SmaI, HindIII, PstI, BglI, NdeI, ApaI, NarI.

Figure 3A:
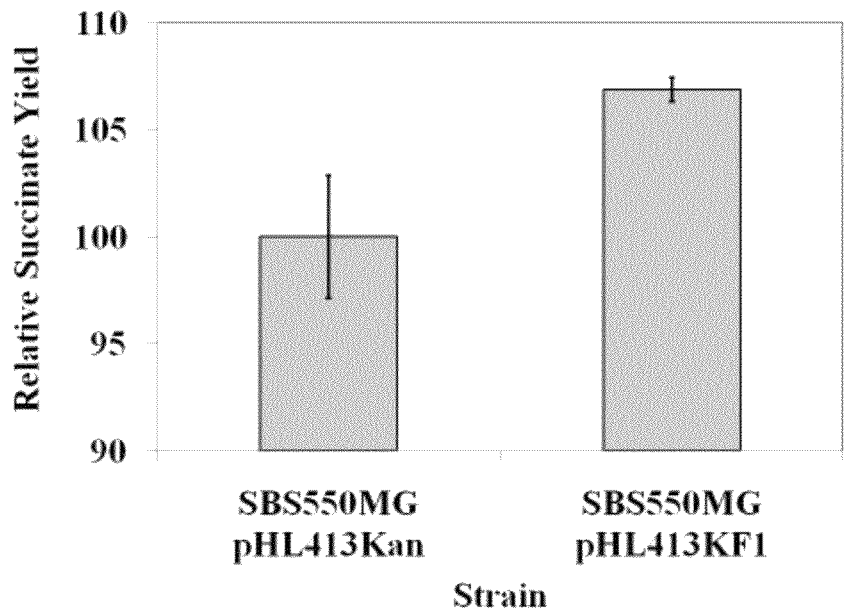
Figure 3B:
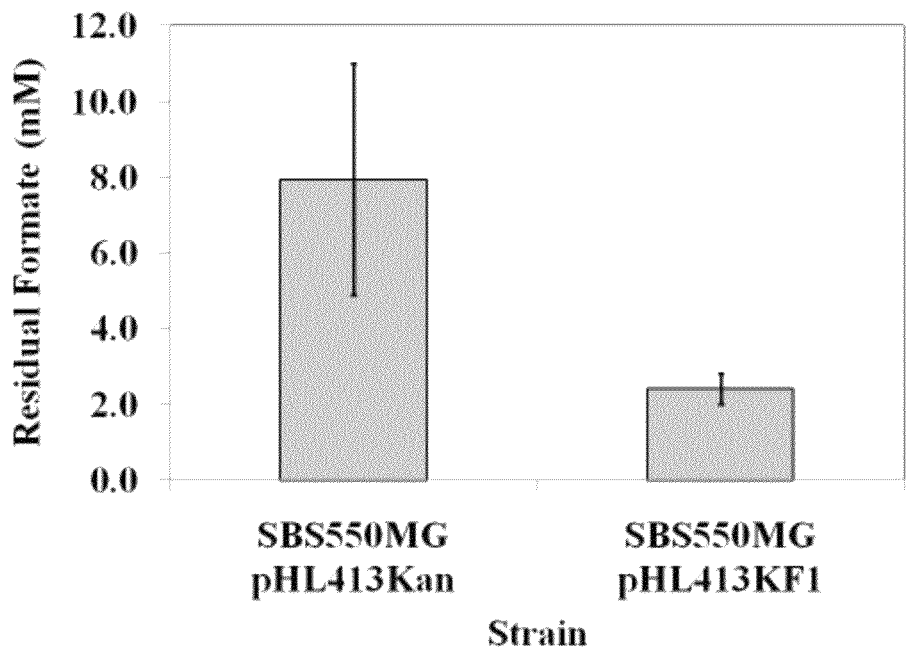

FIG. 3 is metabolite data from anaerobic shake flask fermentation experiments showing the relative succinate yield with the control strain normalized to 100% (A) and the residual formate (mM) (B) using the genetically engineered *E. coli* strain SBS550MG (ΔadhEΔldhAΔiclRΔack-pta) harboring either pHL413Kan (PYC$^+$ overexpressing control vector) or vector pHL413KF1 (PYC$^+$FDH$^+$). The reported values represent averages of HPLC data from at least three independent experiments and error bars indicate the standard error of the means.

FIG. 4 is metabolite data from the anaerobic phase of bioreactor experiments showing the glucose consumption (mM) (A) and the succinate production (mM) (B) over time by the same two mutants.

FIG. 5 is metabolite data from the anaerobic phase of bioreactor experiments showing the succinate production rate (g/L/h) (A) and the residual formate (mM) (B) over time by the same two mutants.

Figure 6A:
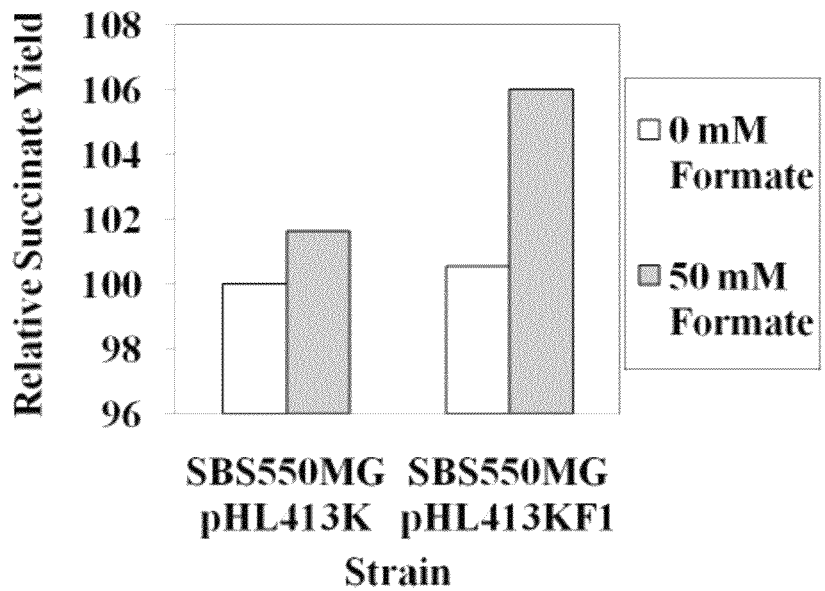
Figure 6B:
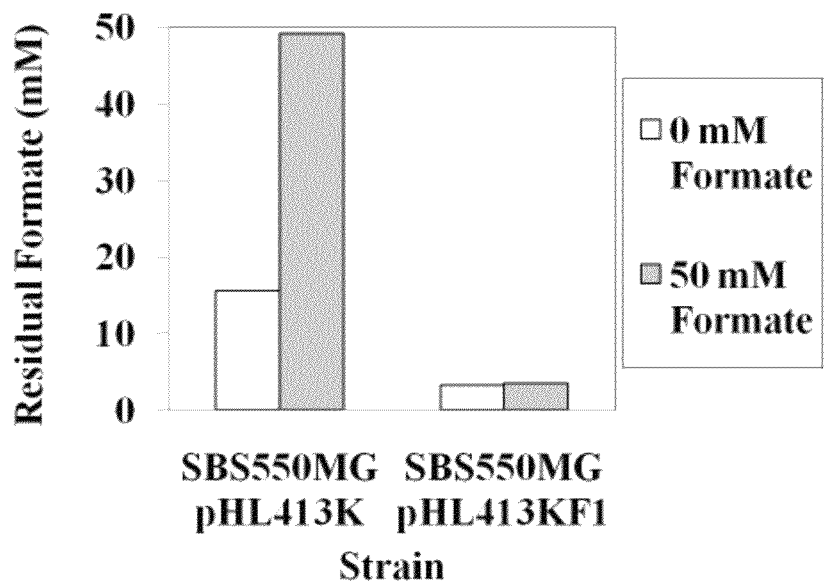

FIG. 6 is metabolite data from anaerobic shake flask fermentation experiments showing the relative succinate yield with the control strain at 0 mM formate normalized to 100% (A) and the residual formate concentration (mM) with and without 50 mM sodium formate supplementation (B). The reported values represent averages of HPLC data from two independent experiments using the same pair of mutants.

FIG. 7. Exemplary FDH sequence SEQ ID NO. 1.
FIG. 8. Exemplary PYC sequence SEQ ID NO. 2.

DESCRIPTION OF EMBODIMENTS OF THE INVENTION

As used herein the specification, "a" or "an" may mean one or more. As used herein in the claim(s), when used in conjunction with the word "comprising", the words "a" or "an" may mean one or more than one. As used herein "another" may mean at least a second or more.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

As used herein, the expressions "cell", "cell line" and "cell culture" are used interchangeably and all such designations include progeny. Thus, the words "cells" and similar designations include the primary subject cell and cultures derived therefrom without regard for the number of transfers. It is also understood that all progeny may not be precisely identical in DNA content, due to deliberate or inadvertent mutations that arise after genetic engineering is concluded. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" is relating to, derived from, or containing genetically engineered material. In other words, the genome was intentionally manipulated in some way.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like.

Overexpression" or "overexpressed" is defined herein to be at least 150% of protein activity as compared with an appropriate control species. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. An overexpressed gene can be represented by the $^+$ symbol, e.g., PYC$^+$.

The terms "disruption" as used herein, refer to cell strains in which the native gene or promoter is mutated, deleted, interrupted, or down regulated in such a way as to decrease the activity of the protein at least 90% over the wild type un-disrupted protein. A gene or protein can be completely (100%) reduced by knockout or removal of the entire genomic DNA sequence. A knockout mutant can be represented by the Δ symbol.

Use of a frame shift mutation, early stop codon, point mutations of critical residues, or deletions or insertions, and the like, can completely inactivate (100%) gene product by completely preventing transcription and/or translation of active protein.

Generally speaking we have referenced protein names herein, but it is understood that a change in protein activity can of course be effected by changing the gene. This provides clarity since the gene nomenclature can be widely divergent in bacteria, but the proteins are defined by their activities and thus names.

The following abbreviations, plasmids and strains are used herein:

| ABBREVIATION | FULL NAME |
|---|---|
| aceBAK operon | Encodes genes required for the glyoxylate bypass and is essential for growth on acetate or fatty acids. Isocitrate lyase and malate synthase are encoded by aceA and aceB, respectively, while isocitrate dehydrogenase (IDH) kinase/phosphatase is encoded by aceK. |
| ACK | acetate kinase |
| ackA | *E. coli* gene encoding ACK |
| ADH | Alcohol dehydrogenase |
| adhE | *E. coli* gene encoding ADH |
| CmR | chloramphenicol resistance gene |
| EtOH | ethanol |
| FDH | Formate dehydrogenase, cofactor dependant |
| iclR | *E. coli* gene encoding ICLR aka aceBAK operon repressor |
| ICLR | the aceBAK operon repressor |
| LDH | lactate dehydrogenase |
| ldhA | *E. coli* gene encoding LDH, NAD$^+$-dependent |
| PTA | Phosphotransacetylase |
| pta | *E. coli* gene encoding PTA |
| PYC | Pyruvate carboxylase |
| pycA | Gene encoding PYC from *Lactococcus lactis* |

| PLASMID AND STRAINS |
|---|
| pHL413Kan - plasmid containing only PYC |
| pHL413KF1 - plasmid containing PYC and FDH (see FIG. 2) |
| SBS550MG - ΔadhEΔldhAΔiclRΔack-pta::CmR |
| SBS550MG pHL413KF1-ΔadhEΔldhAΔiclRΔack-pta::CmR plus overexpressed PYC and FDH |

The following examples are illustrative only, and are not intended to unduly limit the scope of the invention.

EXAMPLE 1

Methods

Disrupted bacteria were prepared according to known techniques, essentially as described in U.S. Pat. No. 7,223,567. Overexpressed PYC and FDH was achieved by combining these two genes on one plasmid as shown in FIG. 2, but the genes can also be added to the bacterial chromosome or added by any other vector or even via separate vectors.

Anaerobic shake flasks experiments were performed at 37° C. with shaking at 250 rpm for 20-24 hours using $CO_2$ purged flasks containing 200 OD units of cells resuspended in 10 ml LB broth supplemented with 20 g/L glucose, 1 g/L $NaHCO_3$, 50 g/L $MgCO_3$, 50 µg/ml kanamycin (FIG. 3), and 50 mM sodium formate (FIG. 6).

Bioreactor experiments were performed using aerobically grown biomass using modified dual-phase medium with 4 g/L glucose unless noted otherwise followed by the anaerobic succinate production phase using 0.2 L/min $CO_2$, 20 g/L glucose, 6.4 g/L $MgCO_3$, 50 µg/ml kanamycin, and 14.3 M $NH_4OH$ to maintain the pH at 7.0 (FIGS. 4 and 5).

EXAMPLE 2

Results

To demonstrate the utility and advantages of the invention, we used the previously engineered high succinate producing *E. coli* strain having ΔadhEΔldhAΔiclRΔack-pta plus $PYC^+$ [strain SBS550MG pHL413Kan]. This strain was further enhanced by adding a $NAD^+$-dependent formate dehydrogenase ($FDH^+$) to regenerate NADH in vivo and manipulate intracellular NADH availability (see dotted box in FIG. 1). The performance of the two strains were then compared.

In previous studies, it was demonstrated that this $NAD^+$-dependent FDH pathway converts 1 mol of formate into 1 mol of NADH and carbon dioxide (Berrios-Rivera et al., 2002a, b, 2004). Implementation of the NADH regeneration system thus doubled the maximum yield of NADH using glucose as a substrate from 2 to 4 mol NADH/mol of substrate consumed in complex medium.

In our experiments, this increase in NADH availability significantly changed the final metabolite concentration pattern under anaerobic conditions. The parent strain used in this demonstration was capable of producing succinate from glucose to a yield of about 1.6 mol/mol with an average anaerobic productivity rate of 10 mM/h (Sanchez et al., 2005), but adding in an $NAD^+$-dependant FDH resulted in much faster average succinate production rate (15 mM/h).

Along with succinate as a major product, the parent strain also produced 12.7 mM of formate during the anaerobic production phase. The overexpressed biologically active $NAD^+$-dependent formate dehydrogenase (FDH) from *Candida boidinii* (FIG. 7) also served to reduce production of formate.

The newly introduced NADH regenerating formate dehydrogenase pathway will provide one mole of NADH from one mole of formate. In contrast, the native formate dehydrogenase converts formate to $CO_2$ and $H_2$ with no cofactor involvement. The new system retains the reducing power of formate resulting in a more robust strain with a much faster average succinate production rate (15 mM/h) and reduced average byproduct formate concentration (3 mM), thereby leading to opportunities for reduced costs associated with downstream processing, purification, and waste disposal.

The functionality of the new succinate production system that regenerates NADH leading to an increase in succinate production rate and decrease in the byproduct formate, was successfully demonstrated in anaerobic shake flask fermentations (FIG. 3, 6) and anaerobic bioreactor experiments (FIGS. 4-5).

An additional feature of the new system was that this $NAD^+$-dependent FDH resulted in an increase in the succinate production yield. As previously mentioned, the new pathway converts 1 mol of formate into 1 mol of NADH and carbon dioxide (Berrios-Rivera et al., 2002a, b, 2004). This conversion can be exploited by supplementing fermentations with external formate thereby providing an additional increase in the NADH availability. A demonstration of the increased succinate yield using externally supplemented formate was performed using shake flask fermentations (FIG. 6). The percentage increase in molar yield is 2-5%.

In summary, the advantages of using the new improved system include:
1. Increased rate of succinate production because of an increase in NADH availability.
2. Reduced levels of byproduct formate due to overexpression of an $NAD^+$-dependent formate dehydrogenase that converts 1 mole of formate into 1 moll of NADH and carbon dioxide.
3. Increased succinate yields using externally supplemented formate because the NAD+-dependent formate dehydrogenase provides additional NADH availability.

The following references are incorporated by reference herein in their entirety.

Berrios-Rivera, S. J., Bennett, G. N., San, K.-Y., 2002a. Metabolic engineering of *Escherichia coli*: increase of NADH availability by overexpressing an NAD+-dependent formate dehydrogenase. Metab. Eng. 4, 217-229.

Berrios-Rivera, S. J., Bennett, G. N., San, K.-Y., 2002b. The effect of increasing NADH availability on the redistribution of metabolic fluxes in *Escherichia coli* chemostat cultures. Metab. Eng. 4, 230-237.

Berrios-Rivera, S. J., Sanchez, A. M., Bennett, G. N., San, K.-Y., 2004 Effect of different levels of NADH availability on metabolite distribution in *Escherichia coli* fermentation in defined and complex media. App. Microbiol. Biotechnol. 65, 426-432.

Lin H., San, K.-Y., Bennett, G. N. 2005. Effect of *Sorghum vulgare* phosphoenolpyruvate carboxylase and *Lactococcus lactis* pyruvate carboxylase coexpression on succinate production in mutant strains of *Escherichia coli*. Appl. Microbiol. Biotechnol. 67, 515-523.

Sakai, Y., Murdanato, A. P., Konishi, T., Iwamatsu, A., Kato, N., 1997. Regulation of the formate dehydrogenase gene, FDH1, in the methylotrophic yeast *Candida boidinii* and growth characteristics of an FDH1-disrupted strain on methanol, methylamine, and choline. J. Bacteriol. 179, 4480-4485.

Sanchez, A. M., Bennett, G. N., San, K.-Y., 2005. Novel pathway engineering design of the anaerobic central metabolic pathway in *Escherichia coli* to increase succinate yield and productivity. Metab. Eng. 7, 229-239.

Vemuri, G. N., Eiteman, M. A., Altman, E., 2002. Effects of growth mode and pyruvate carboxylase on succinic acid production by metabolically engineered strains of *Escherichia coli*. Appl. Environ. Microbiol. 68, 1715-1727.

What is claimed is:

1. An engineered *E. coli* comprising reduced activity of alcohol dehydrogenase (ADH), reduced activity of lactate dehydrogenase (LDH), reduced activity of acetate kinase (ACK) or phosphotransacetylase (PTA) or both (ACK-PTA), reduced activity of the aceBAK operon repressor (ICLR) and overexpressed NAD$^+$-dependent formate dehydrogenase (FDH$^+$) and overexpressed pyruvate carboxylase (PYC$^+$).

2. The *E. coli* of claim 1, wherein said *E. coli* comprising ΔadhE, Δldh, Δack-pta, ΔiclR and FDH⁺ and PYC⁺.

3. The *E. coli* of claim 1, wherein the FDH has at least 65% identity to SEQ ID NO 1.

4. The *E. coli* of claim 1, wherein the PYC has at least 63% identity to SEQ ID NO. 2.

5. The *E. coli* of claim 1, wherein the FDH has SEQ ID NO 1.

6. The *E. coli* of claim 1, wherein the PYC has SEQ ID NO. 2.

7. The *E. coli* of claim 2, wherein the FDH has at least 65% identity to SEQ ID NO 1.

8. The *E. coli* of claim 2, wherein the PYC has at least 63% identity to SEQ ID NO. 2.

9. The *E. coli* of claim 2, wherein the FDH has SEQ ID NO 1.

10. The *E. coli* of claim 2, wherein the PYC has SEQ ID NO. 2.

11. A method of making a four carbon dicarboxylic acid from the Krebs cycle, comprising culturing the *E. coli* of any one of claim 1-10 in a medium, and isolating a four carbon dicarboxylic acid from said *E. coli* or medium or both.

12. A method of making a succinate, comprising culturing the *E. coli* of any one of claim 1-10 in a medium, and isolating succinate from said *E. coli* or medium or both.

13. The method of claim 11, further comprising supplementing said medium with 25-250 mM formate.

14. The method of claim 12, further comprising supplementing said medium with 25-250 mM formate.

15. The method of claim 12, wherein the yield of succinate is >1.6 moles/mole of glucose.

16. The method of claim 14, wherein the yield of succinate is >1.7 moles/mole of glucose.

17. The method of claim 11, wherein the *E. coli* comprising ΔadhE, Δldh, Δack-pta, ΔiclR and FDH⁺ and PYC⁺.

* * * * *

SEQUENCE LISTING

<160> NUMBER OF SEQ ID NOS: 2

<210> SEQ ID NO 1
<211> LENGTH: 364
<212> TYPE: PRT
<213> ORGANISM: Candida boidinii
<300> PUBLICATION INFORMATION:
<308> DATABASE ACCESSION NUMBER: CAA0946
<309> DATABASE ENTRY DATE: 2005-04-15
<313> RELEVANT RESIDUES IN SEQ ID NO: (1)..(364)

<400> SEQUENCE: 1

```
Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Gly Asn Ser Val Leu Asp Gln His Ile Pro Asp Ala Asp Ile Ile
    50                  55                  60

Ile Thr Thr Pro Phe His Pro Ala Tyr Ile Thr Lys Glu Arg Ile Asp
65                  70                  75                  80

Lys Ala Lys Lys Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Val Pro Phe Asn Pro Lys Glu Leu Leu
            180                 185                 190

Tyr Tyr Asp Tyr Gln Ala Leu Pro Lys Asp Ala Glu Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Gln Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350
```

Tyr Val Thr Lys Ala Tyr Gly Lys His Asp Lys Lys
            355                 360

<210> SEQ ID NO 2
<211> LENGTH: 1137
<212> TYPE: PRT
<213> ORGANISM: Lactococcus lactis subsp. lactis
<300> PUBLICATION INFORMATION:
<308> DATABASE ACCESSION NUMBER: AF068759
<309> DATABASE ENTRY DATE: 2000-03-01
<313> RELEVANT RESIDUES IN SEQ ID NO: (1)..(1137)

<400> SEQUENCE: 2

Met Lys Lys Leu Leu Val Ala Asn Arg Gly Glu Ile Ala Val Arg Val
1               5                   10                  15

Phe Arg Ala Cys Asn Glu Leu Gly Leu Ser Thr Val Ala Val Tyr Ala
            20                  25                  30

Arg Glu Asp Glu Tyr Ser Val His Arg Phe Lys Ala Asp Glu Ser Tyr
        35                  40                  45

Leu Ile Gly Gln Gly Lys Lys Pro Ile Asp Ala Tyr Leu Asp Ile Asp
    50                  55                  60

Asp Ile Ile Arg Val Ala Leu Glu Ser Gly Ala Asp Ala Ile His Pro
65                  70                  75                  80

Gly Tyr Gly Leu Leu Ser Glu Asn Leu Glu Phe Ala Thr Lys Val Arg
                85                  90                  95

Ala Ala Gly Leu Val Phe Val Gly Pro Glu Leu His His Leu Asp Ile
            100                 105                 110

Phe Gly Asp Lys Ile Lys Ala Lys Ala Ala Asp Glu Ala Gln Val
        115                 120                 125

Pro Gly Ile Pro Gly Thr Asn Gly Ala Val Asp Ile Asp Gly Ala Leu
    130                 135                 140

Glu Phe Ala Gln Thr Tyr Gly Tyr Pro Val Met Ile Lys Ala Ala Leu
145                 150                 155                 160

Gly Gly Gly Gly Arg Gly Met Arg Val Ala Arg Asn Asp Ala Glu Met
                165                 170                 175

His Asp Gly Tyr Ala Arg Ala Lys Ser Glu Ala Ile Gly Ala Phe Gly
            180                 185                 190

Ser Gly Glu Ile Tyr Val Glu Lys Tyr Ile Glu Asn Pro Lys His Ile
        195                 200                 205

Glu Val Gln Ile Leu Gly Asp Ser His Gly Asn Ile Val His Leu His
    210                 215                 220

Glu Arg Asp Cys Ser Val Gln Arg Arg Asn Gln Lys Val Ile Glu Ile
225                 230                 235                 240

Ala Pro Ala Val Gly Leu Ser Pro Glu Phe Arg Asn Glu Ile Cys Glu
                245                 250                 255

Ala Ala Val Lys Leu Cys Lys Asn Val Gly Tyr Val Asn Ala Gly Thr
            260                 265                 270

Val Glu Phe Leu Val Lys Asp Asp Lys Phe Tyr Phe Ile Glu Val Asn
        275                 280                 285

Pro Arg Val Gln Val Glu His Thr Ile Thr Glu Leu Ile Thr Gly Val
    290                 295                 300

Asp Ile Val Gln Ala Gln Ile Leu Ile Ala Gln Gly Lys Asp Leu His
305                 310                 315                 320

Thr Glu Ile Gly Ile Pro Ala Gln Ala Glu Ile Pro Leu Leu Gly Ser
                325                 330                 335

```
Ala Ile Gln Cys Arg Ile Thr Thr Glu Asp Pro Gln Asn Gly Phe Leu
            340                 345                 350

Pro Asp Thr Gly Lys Ile Asp Thr Tyr Arg Ser Pro Gly Gly Phe Gly
        355                 360                 365

Ile Arg Leu Asp Val Gly Asn Ala Tyr Ala Gly Tyr Glu Val Thr Pro
    370                 375                 380

Tyr Phe Asp Ser Leu Leu Val Lys Val Cys Thr Phe Ala Asn Glu Phe
385                 390                 395                 400

Ser Asp Ser Val Arg Lys Met Asp Arg Val Leu His Glu Phe Arg Ile
                405                 410                 415

Arg Gly Val Lys Thr Asn Ile Pro Phe Leu Ile Asn Val Ile Ala Asn
            420                 425                 430

Glu Asn Phe Thr Ser Gly Gln Ala Thr Thr Thr Phe Ile Asp Asn Thr
        435                 440                 445

Pro Ser Leu Phe Asn Phe Pro Arg Leu Arg Asp Arg Gly Thr Lys Thr
    450                 455                 460

Leu His Tyr Leu Ser Met Ile Thr Val Asn Gly Phe Pro Gly Ile Glu
465                 470                 475                 480

Asn Thr Glu Lys Arg His Phe Glu Glu Pro Arg Gln Pro Leu Leu Asn
                485                 490                 495

Ile Glu Lys Lys Lys Thr Ala Lys Asn Ile Leu Asp Glu Gln Gly Ala
            500                 505                 510

Asp Ala Val Val Glu Tyr Val Lys Asn Thr Lys Glu Val Leu Leu Thr
        515                 520                 525

Asp Thr Thr Leu Arg Asp Ala His Gln Ser Leu Leu Ala Thr Arg Leu
    530                 535                 540

Arg Leu Gln Asp Met Lys Gly Ile Ala Gln Ala Ile Asp Gln Gly Leu
545                 550                 555                 560

Pro Glu Leu Phe Ser Ala Glu Met Trp Gly Gly Ala Thr Phe Asp Val
                565                 570                 575

Ala Tyr Arg Phe Leu Asn Glu Ser Pro Trp Tyr Arg Leu Arg Lys Leu
            580                 585                 590

Arg Lys Leu Met Pro Asn Thr Met Phe Gln Met Leu Phe Arg Gly Ser
        595                 600                 605

Asn Ala Val Gly Tyr Gln Asn Tyr Pro Asp Asn Val Ile Glu Glu Phe
    610                 615                 620

Ile His Val Ala Ala His Glu Gly Ile Asp Val Phe Arg Ile Phe Asp
625                 630                 635                 640

Ser Leu Asn Trp Leu Pro Gln Met Glu Lys Ser Ile Gln Ala Val Arg
                645                 650                 655

Asp Asn Gly Lys Ile Ala Glu Ala Thr Ile Cys Tyr Thr Gly Asp Ile
            660                 665                 670

Leu Asp Pro Ser Arg Pro Lys Tyr Asn Ile Gln Tyr Tyr Lys Asp Leu
        675                 680                 685

Ala Lys Glu Leu Glu Ala Thr Gly Ala His Ile Leu Ala Val Lys Asp
    690                 695                 700

Met Ala Gly Leu Leu Lys Pro Gln Ala Ala Tyr Arg Leu Ile Ser Glu
705                 710                 715                 720

Leu Lys Asp Thr Val Asp Leu Pro Ile His Leu His Thr His Asp Thr
                725                 730                 735

Ser Gly Asn Gly Ile Ile Thr Tyr Ser Gly Ala Thr Gln Ala Gly Val
            740                 745                 750

Asp Ile Ile Asp Val Ala Thr Ala Ser Leu Ala Gly Gly Thr Ser Gln
```

```
                    755                 760                 765
Pro Ser Met Gln Ser Ile Tyr Tyr Ala Leu Glu His Gly Pro Arg His
    770                 775                 780

Ala Ser Ile Asn Val Lys Asn Ala Glu Gln Ile Asp His Tyr Trp Glu
785                 790                 795                 800

Asp Val Arg Lys Tyr Tyr Ala Pro Phe Glu Ala Gly Ile Thr Ser Pro
                805                 810                 815

Gln Thr Glu Val Tyr Met His Glu Met Pro Gly Gly Gln Tyr Thr Asn
                820                 825                 830

Leu Lys Ser Gln Ala Ala Val Gly Leu Gly His Arg Phe Asp Glu
                835                 840                 845

Ile Lys Gln Met Tyr Arg Lys Val Asn Met Met Phe Gly Asp Ile Ile
    850                 855                 860

Lys Val Thr Pro Ser Ser Lys Val Val Gly Asp Met Ala Leu Phe Met
865                 870                 875                 880

Ile Gln Asn Glu Leu Thr Glu Glu Asp Val Tyr Ala Arg Gly Asn Glu
                885                 890                 895

Leu Asn Phe Pro Glu Ser Val Val Ser Phe Phe Arg Gly Asp Leu Gly
                900                 905                 910

Gln Pro Val Gly Gly Phe Pro Glu Glu Leu Gln Lys Ile Ile Val Lys
                915                 920                 925

Asp Lys Ser Val Ile Met Asp Arg Pro Gly Leu His Ala Glu Lys Val
    930                 935                 940

Asp Phe Ala Thr Val Lys Ala Asp Leu Glu Gln Lys Ile Gly Tyr Glu
945                 950                 955                 960

Pro Gly Asp His Glu Val Ile Ser Tyr Ile Met Tyr Pro Gln Val Phe
                965                 970                 975

Leu Asp Tyr Gln Lys Met Gln Arg Glu Phe Gly Ala Val Thr Leu Leu
                980                 985                 990

Asp Thr Pro Thr Phe Leu His Gly Met Arg Leu Asn Glu Lys Ile Glu
                995                 1000                1005

Val Gln Ile Glu Lys Gly Lys Thr Leu Ser Ile Arg Leu Asp Glu
    1010                1015                1020

Ile Gly Glu Pro Asp Leu Ala Gly Asn Arg Val Leu Phe Phe Asn
    1025                1030                1035

Leu Asn Gly Gln Arg Arg Glu Val Val Ile Asn Asp Gln Ser Val
    1040                1045                1050

Gln Thr Gln Ile Val Ala Lys Arg Lys Ala Glu Thr Gly Asn Pro
    1055                1060                1065

Asn Gln Ile Gly Ala Thr Met Pro Gly Ser Val Leu Glu Ile Leu
    1070                1075                1080

Val Lys Ala Gly Asp Lys Val Lys Lys Gly Gln Ala Leu Met Val
    1085                1090                1095

Thr Glu Ala Met Lys Met Glu Thr Thr Ile Glu Ser Pro Phe Asp
    1100                1105                1110

Gly Glu Val Ile Ala Leu His Val Val Lys Gly Glu Ala Ile Gln
    1115                1120                1125

Thr Gln Asp Leu Leu Ile Glu Ile Asp
    1130                1135
```